(12) United States Patent
Guglielmi

(10) Patent No.: US 6,620,152 B2
(45) Date of Patent: Sep. 16, 2003

(54) METHOD AND APPARATUS FOR FAST ELECTROLYITIC DETACHMENT OF AN IMPLANT

(75) Inventor: Guido Guglielmi, Rome (IT)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/170,897

(22) Filed: Jun. 13, 2002

(65) Prior Publication Data

US 2002/0151883 A1 Oct. 17, 2002

Related U.S. Application Data

(63) Continuation of application No. 09/450,033, filed on Nov. 24, 1999, now Pat. No. 6,425,893, which is a continuation-in-part of application No. 08/647,114, filed on May 9, 1996, now Pat. No. 6,083,220, which is a division of application No. 08/485,821, filed on Jun. 6, 1995, now abandoned, which is a continuation of application No. 07/840,211, filed on Feb. 24, 1992, now Pat. No. 5,354,295, which is a continuation-in-part of application No. 07/492,717, filed on Mar. 13, 1990, now Pat. No. 5,122,136.

(51) Int. Cl.7 ............................................. A61B 17/00
(52) U.S. Cl. ................................. 606/1; 606/1; 606/32
(58) Field of Search ............................ 606/1, 32, 108, 606/191; 623/1, 15

(56) References Cited

U.S. PATENT DOCUMENTS

| | | | | |
|---|---|---|---|---|
| 5,354,295 A | * | 10/1994 | Guglielmi et al. | 606/32 |
| 5,891,128 A | * | 4/1999 | Gia et al. | 606/1 |
| 5,964,797 A | * | 10/1999 | Ho | 623/1.15 |
| 5,984,929 A | * | 11/1999 | Bashiri et al. | 606/108 |
| 6,077,260 A | * | 6/2000 | Wheelock et al. | 606/32 |
| 6,165,178 A | * | 12/2000 | Bashiri et al. | 606/108 |
| 6,193,708 B1 | * | 2/2001 | Ken et al. | 606/1 |

* cited by examiner

Primary Examiner—Lee Cohen
(74) Attorney, Agent, or Firm—Daniel L. Dawes; Myers Dawes Andras & Sherman LLP

(57) ABSTRACT

This is an implant for placement in the human body and a wire coupled to the implant for placing that implant. In the illustrated embodiment, it is an implant for use in the vasculature of the human body and is used to occlude a cavity in that vasculature as a portion of a treatment regimen. The implant itself is a component of a deployment device in which the implant is detached from the wire using electrolytic disintegration when a current is applied to the wire. The implant is electrically isolated from active participation in the electrolytic disintegration which occurs when a current is applied to the wire. Such isolation and minimization of the conductive pathway from the placement apparatus to the body's fluids appears to enhance the susceptibility of a selected portion of the wire to electrolysis to provide for quick erosion and detachment of the implant from the wire. Although the implant itself is preferably a vaso-occlusive device, it may instead be used for any implant which may be installed in this manner.

9 Claims, 4 Drawing Sheets

METHOD AND APPARATUS FOR FAST ELECTROLYITIC DETACHMENT OF AN IMPLANT

RELATED APPLICATIONS

The present application is a continuation of application Ser. No. 09/450,033, filed on Nov. 24, 1999, now issued as U.S. Pat. No. 6,425,893, issued on July 30, 2002, which was a continuation-in-part application of application Ser. No. 08/647,114, filed May 9, 1996, which issued as U.S. Pat. No. 6,083,220, which is a divisional of application Ser. No. 08/485,821 filed Jun. 6, 1995, now abandoned, which in turn was a continuation of application Ser. No. 07/840,211, filed on Feb. 24, 1992, issued as U.S. Pat. No. 5,354,295, which in turn was a continuation-in-part application of application Ser. No. 07/492,717 filed Mar. 13, 1990, issued as U.S. Pat. No. 5,122,136, all of which are incorporated herein by reference.

BACKGROUND OF THE INVENTION

1. Field of Invention

This invention is an implant for placement in the human body and an assembly for so placing that implant. Most desirably, it is an implant for use in the vasculature of the human body and is used to occlude a cavity or space in that vasculature as a portion of a treatment regimen. The implant itself is preferably a component of a deployment device or assembly using an electrolytically severable joint or a selected portion of a wire connected to the implant.

2. Description of the Prior or Related Art

Implants may be placed in the human body for a wide variety of reasons. For instance, stents are placed in a number of different lumens in the body. They may be placed in arteries to cover vascular lesions or to provide patency to the vessel. Stents are also placed in biliary ducts to prevent them from kinking or collapsing. Grafts may be used with stents to promote growth of endothelial tissue within those vessels. Vena cava filters are implanted in the body, typically in the vena cava, to catch thrombus which are sloughed off from other sites within the body and which may be in the blood passing through the chosen site.

Vaso-occlusive devices or implants are used for a wide variety of reasons. They are often used for treatment of intra-vascular aneurysms. This is to say that the treatment involves the placement of a vaso-occlusive device in an aneurysm to cause the formation of a clot and eventually of a collagenous mass containing the vaso-occlusive device. These occlusions seal and fill the aneurysm thereby preventing the weakened wall of the aneurysm from being exposed to the pulsing blood pressure of the open vascular lumen.

Treatment of aneurysms in this fashion is a significant improvement over the surgical method typically involved. The surgical or extravascular approach is a common treatment of intracranial berry aneurysm; it is straightforward but fairly traumatic. The method involves removing of portion of the cranium and locating the aneurysm. The neck of the aneurysm is closed typically by applying a specially sized clip to the neck of the aneurysm. The surgeon may choose to perform a suture ligation of the neck or wrap the entire aneurysm. Each of these procedures is performed by an very intrusive invasion into the body and is performed from the outside of the aneurysm or target site. General anesthesia, craniotomy, brain retraction, and a placement of clip around the neck of the aneurysm all are traumatic. The surgical procedure is often delayed while waiting for the patient to stabilize medically. For this reason, many patients die from the underlying disease prior to the initiation of the surgical procedure.

Another procedure—the extra—intravascular approach—involves surgically exposing or stereotaxically reaching an aneurysm with a probe. The wall of the aneurysm is perforated from the outside and various techniques are used to occlude the interior of the aneurysm to prevent its rebleeding. The techniques used to occlude the aneurysm include electro-thrombosis, adhesive embolization, hoghair embolization, and ferromagnetic thrombosis. These procedures are discussed in U.S. Pat. No. 5,122,136 to Guglielmi et al., the entirety of which is incorporated by reference.

Guglielmi further describes an endovascular procedure which is at once the most elegant and least invasive. The procedure described in that patent includes a step in which the interior of the aneurysm is entered by the use of guidewire such as those in Engelson, U.S. Pat. No. 4,884,579 and a catheter as in Engelson, U.S. Pat. No. 4,739,768. These patents described devices utilizing guidewires and catheters which allow access to aneurysms from remote parts of the body. Typically, these catheters enter the vasculature through the femoral artery in the groin. The Guglielmi system uses catheters and core wires which have a very flexible distal regions and supporting midsections which allow the combinations to be steerable to the region of the aneurysm. That is to say that the guidewire is first steered for a portion of the route to the aneurysm and the catheter is slid up over that guidewire until it reaches a point near the distal end of the guidewire. By steps, the catheter and guidewire are then placed at the mouth of the aneurysm. The catheter is introduced into the aneurysm and vaso-occlusive or embolism forming devices may be delivered through the lumen.

Various vaso-occlusive devices are introduced through the noted microcatheters to close the aneurysm site. In some instances, a small balloon may be introduced into the aneurysm where it is inflated, detached, and left to occlude the aneurysm. Balloons are becoming less in favor because of the difficulty in introducing the balloon into the aneurysm sac, the possibility of aneurysm rupture due to over-inflation of the balloon within the aneurysm, and the inherent risk associated with the traction produced when detaching the balloon.

Another desirable embolism-forming device which may be introduced into aneurysm using end of vascular placement procedure is found in U.S. Pat. No. 4,994,069 to Ritchart et al. In that patent are described various devices, typically platinum/tungsten alloy coils having very small diameters, which may be introduced into the aneurysm through a catheter such as those described in the Engelson patents above. These coils are often made of wire having a diameter of 2–6 mils. The coil diameter is often 10–30 mils. These soft, flexible coils, may be of any length desirable and appropriate for the site to be occluded. After these vaso-occlusive coils are placed in a berry aneurysm, for example, they first cause a formation of an embolic mass. This initial mass or clot is thereafter complemented with a collagenous material which significantly lessens the potential for aneurysm rupture.

There are variety of other vaso-occlusive devices, typically coils which may be delivered to the vascular site in a variety of ways, e.g., by mechanically detaching them from the delivery device. For instance, U.S. Pat. No. 5,234,437, to Sepetka shows a method of unscrewing a helically wound coil from a pusher having interlocking surfaces. U.S. Pat.

No. 5,250,071, to Palermo shows an embolic coil assembly using interlocking clasps both on the pusher and on the embolic coil. U.S. Pat. No. 5,261,916, to Engelson shows a combination pusher/vasoocclusive coil assembly joined by an interlocking ball and keyway type coupling. U.S. Pat. No. 5,304,195, to Twyford et al., shows a pusher/vaso-occlusive coil assembly having a fixed proximally extending wire carrying a ball on its proximal end and a pusher having a similar end which two tips are interlocked and disengaged when expelled from the distal tip of the catheter. U.S. Pat. No. 5,312,415, to Palermo shows a method for discharging numerous coils from a single pusher by using a guidewire which has a section capable of interconnecting with the interior of a helically wound coil. U.S. Pat. No. 5,350,397, to Palermo et al. shows a pusher having a throat at its distal end and a pusher through its axis. The pusher throat holds onto the end of an embolic coil and releases that coil upon pushing the axially placed pusher wire against member found on the proximal end of the vaso-occlusive coil. Other mechanically detachable embolism forming devices are known in the art.

Each of the patents listed herein is specifically incorporated by reference.

Guglielmi et al. shows an embolism forming device and procedure for using that device which, instead of a mechanical joint, uses an electrolytically severable joint. Specifically, Guglielmi places a finely wound platinum coil into a vascular cavity such as an aneurysm. The coil is delivered endovascularly using a catheter such as those described above. After placement in the aneurysm, the coil is severed from its insertion core wire by the application of a small electric current to that core wire. The deliverable coils are said to be made of a platinum material. They may be 1–50 cm or longer as is necessary. Proximal of the embolic coil, as noted above, is a core wire which is typically stainless steel. The core wire is used to push the platinum embolic coil into vascular site to be occluded. Other embodiments of the Guglielmi technology is found in U.S. Pat. No. 5,354,295 (hereinafter referenced as the "Guglielmi system").

BRIEF SUMMARY OF THE INVENTION

This invention is an implant for placement in the human body and an assembly for so placing that implant. In the illustrated embodiment it is an implant for use in the vasculature of the human body and is used to occlude a cavity or space in that vasculature as a portion of a treatment regimen. The implant itself is preferably a component of a deployment device or assembly using an electrolytically severable joint or a selected portion of a wire connected to the implant. The implant is electrically isolated from participating in the electrolysis by electrical insulation between an electrolytically severable joint or portion of the wire by a highly resistive or insulative coupling or by coating of the implant by an a layer of insulation. Such isolation and minimization of the conductive pathway from the placement apparatus to the body's fluids appears to enhance the susceptibility of the electrolytic joint to quick erosion and detachment of the implant from the deployment media. Although the implant itself is preferably a vaso-occlusive device, it may instead be used for any implantable device which may be installed in this manner.

The improvement involves the use of an insulative or highly resistive member proximal of the implant. The resistive or insulating member may be any suitable material such as inorganic oxides, glues, polymeric inserts, polymeric coverings, etc. This insulative or highly resistive layer or joint appears to focus the current flow through the sacrificial electrolytic joint and thereby improves the rate at which detachment of the implant occurs.

More specifically, the invention is an implant assembly for placement of an implant in the human body in presence of an ionic fluid. An electrolytically severable joint is situated to release the implant member upon application of electrical energy to the electrolytically severable joint. The implant member is electrically isolated from electrolysis in the ionic fluid.

In one embodiment, the electrical isolation from electrolysis is due to an insulative or highly resistive layer interposed between implant member and the electrolytically severable joint. The insulative or highly resistive layer may be comprised of a polymer, such as polyester. The layer may be comprised of any material or combinations of materials now known or later devised which in the aggregate are nonconductive or at least highly resistive. For example, the layer may be a drop, plug, fitting, painted coating or any other disposition of material or materials coupling the wire and the joint.

In another embodiment, the electrical isolation from electrolysis is due to an insulative or highly resistive layer coating all exposed surfaces of the implant member.

In the illustrated embodiment, the implant member comprises a helically wound coil of metal, namely an alloy of platinum. However, the implant may have any physical structure or composition compatible with implantation in the human body.

The invention can alternatively be defined as an apparatus for occluding a body cavity in the presence of an ionic fluid comprising a wire whose distal end is adapted to be positioned in or near the body cavity. The distal end of the wire is fully insulated except for a selected portion serving as an electrolytic joint. Thus, the joint may be a separate structure coupled to the wire, may be a modified portion of the wire itself, or may be an integral part of the wire without modification. A detachable implant is coupled to the distal end of the wire, distal from the joint. The implant is adapted to be positioned in the body cavity. The implant is electrically isolated from electrolysis in the ionic fluid. Substantially only the joint is electrolyzed when current is applied to the wire.

Still further the invention can be defined as an apparatus for occluding a body cavity in the presence of an ionic fluid comprising a wire with a distal end which is insulated. An electrolytic joint is coupled to the distal end. The electrolytic joint is insulated at least in part. A detachable implant is coupled to the electrolytic joint. The implant is not subject to electrolysis in the ionic fluid when current is applied to the wire. The joint is electrolyzed when current is applied to the wire to separate the implant from the wire. The wire and implant may or may not be contiguous with each other, or there may be interlying structures therebetween coupling them together, such as the joint or other structures in the case where the joint is not part of the wire.

The invention is also defined as a method for introduction of an implant into a space within the human body comprising the steps of placing a delivery catheter distal tip near the space within the human body, and introducing an implant assembly. The assembly comprises the implant member and an electrolytically severable joint attached to the implant member's proximal end. The implant member is electrically isolated from electrolysis. The method includes the steps of placing the implant member into the space, and electrolytically detaching the implant member from the implant assembly.

The invention now having been briefly summarized, turn to the following drawings where like elements are referenced by like numerals.

The invention now having been depicted in the foregoing drawings, turn to the following detailed description of various embodiments illustrating the invention in various embodiments.

DETAILED DESCRIPTION OF THE PREFERRED EMBODIMENTS

As noted above, the Guglielmi system for deploying an implant into the human body uses a core wire, an electrolytic sacrificial joint, and the implant to be deployed. A power supply is needed to provide power for electrolysis of the joint. The core wire is typically insulated on its outer surface from near the proximal end of the wire and along the wire to the electrolytic sacrificial joint by means of an insulating covering or jacket. In some embodiments the implant forms a portion of the circuit through the body.

This invention substantially removes the implant itself from that circuit thereby increasing the current density at the electrolytic joint or at a selected exposed portion of the wire where it is needed for electrolysis.

Figure 1:
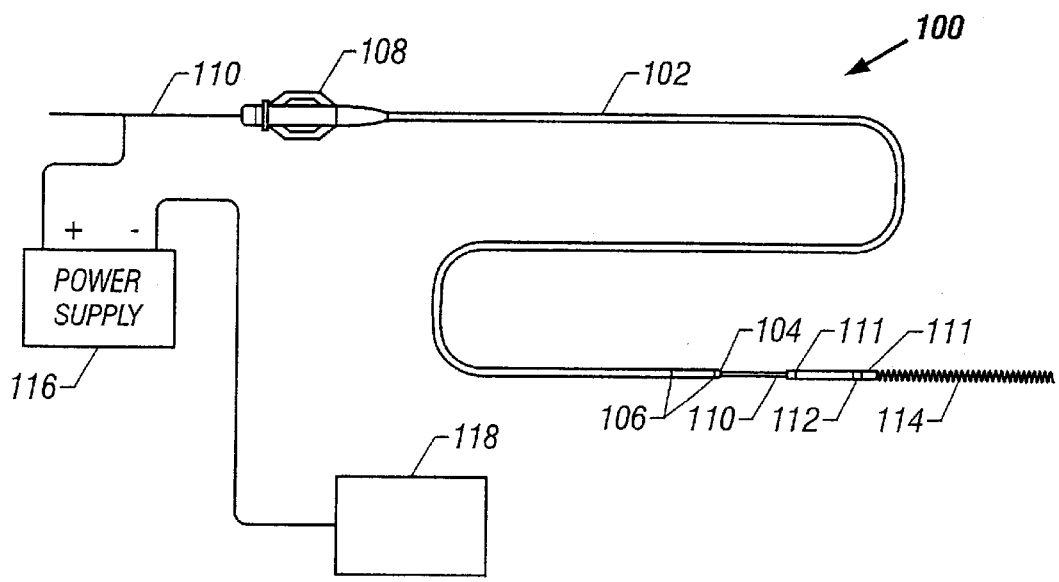
FIG. 1 shows the overall layout of delivery system showing the typical major parts for delivering an implant using the improvement of this invention.

FIG. 1 shows a system for introducing and deploying the implant made according to the invention. The system (100) includes a catheter (102) which is made up of an elongate tubular member, typically made from a polymeric material and often reinforced with a coil or braid to provide strength or obviate kinking propensities. Catheter (102) is shown with a pair of radioopaque markers (106). The radioopaque markers (106) allow visualization of the distal end (104) of the catheter to compare its position with the implant. Catheter (102) is also shown with a proximal fitting (108) for introduction of dyes or treatment materials.

Within the lumen of catheter (102) is a core wire (110) extending both proximally of catheter (102) and distally. Wire (110) is insulated by a nonconducting jacket or coating (111). On the distal end of core wire (110) may be seen the electrolytic joint or exposed portion (112) and the implant (114). Electrolytic joint or exposed portion (112) may comprise simply a selected distal portion of wire (110), or a reduced diameter section of wire (110) from which insulation (111) has been removed or never disposed.

In this instance, implant (114) is shown to be a helically wound vaso-occlusive coil. However, it must be understood that implant (114) may be any type of implantable object which has the capability of being electrolyzed if it were electrically communicated in a circuit from wire (110) to the surrounding blood or ionic fluid. Generally, all of core wire (110) is electrically insulated from a point near the proximal end of core wire (110) continuously to electrolytically severable joint or a selected exposed portion (112) of wire (110). Electrolytically joint or a selected exposed portion (112) is bare and is relatively more susceptible to electrolysis in an ionic solution such as bloods or most other bodily fluids than is the implant (114).

The most proximal end of core wire (110) is also left bare so that power supply (116) may be attached. The other pole of the power supply (116) is typically attached to a patch or body electrode (118). The patch is placed on the skin to complete the circuit from the power supply (116), through the core wire (110), through electrolytic joint (112), through the ionic solution in the body, and back to a patch (118) to the power supply (116). Other return routes may be used as the designer sees fit including tip electrodes on the catheter itself.

Central to this invention is electrical isolation of implant (114) from electrolytic action. This is accomplished in two ways. First, core wire (110) and electrolytically severable joint (112) can be electrically isolated from implant (114). Second, implant (114) can be electrically isolated from the blood or ionic fluid in which it is immersed. Without being bound by an assumed theory of operation, it is believed that isolation of the implant (114) from electrolytic action prevents or lessens current flow through the implant (114) itself and concentrates the current flow or increases the current density through the electrolytic joint or exposed portion (112) of the wire.

Figure 2:
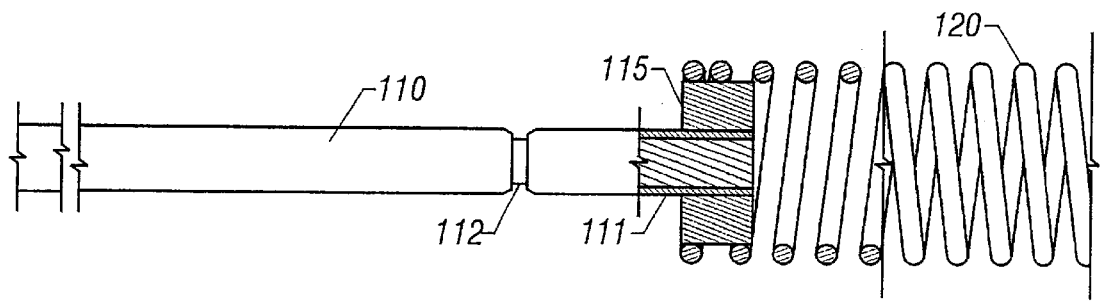
FIGS. 2, 3a and 3b show cross sections depicting various insulating or resistive joints which isolate implants from electrolysis.

FIG. 2 shows a close-up of the more distal portion of one embodiment of the invention. This embodiment includes the core wire (110) and the attached implant (120). Typically, core wire (110) will be conductive but covered with a insulative layer (111) both proximal and distal of electrolytically severable joint (112). Core wire (110) is physically attached to implant (120). In this embodiment of the invention, implant (120) is a helically wound coil.

In this invention, a highly resistive or insulative layer or member electrically isolates implant (120) from core wire (110). In this embodiment of the invention, the insulating layer (111) on the core wire (110) is simply continued to the end of the core wire (110).

An optional bushing (115) may be placed on the core wire (110) to further separate it from implant (120). Optional bushing (115) may be of any suitable material since it operates merely as a spacer. Insulating layer (111) may be any nonconducting, biocompatible material now known or later devised, but preferably is polymeric.

Alternatively, a polyester bead may be used to connect wire (110) to implant (114) as shown in Guglielmi '295, which has been incorporated herein by reference. In the preferred embodiment, coil (120) is mechanically coupled to wire (110) by means of a small drop or bushing of polyester 115. Polyester may be substituted for the gold solder of previously versions of the device. Since polyester is nonconducting, implant (120) is necessarily electrically isolated from wire (110). For example, bushing 115 described above in connection with FIG. 2 may be substituted for a polyester drop or bead connecting wire 110 to implant (120).

The coil making up this embodiment (and other coil-based embodiments) of the invention is generally of a diameter in the range of 0.00025 inches and 0.006 inches. Wire of such diameter is wound into a primary form having a diameter of between 0.003 and 0.025 inches. For most neurovascular indications, the preferable primary coil diameter is preferably between 0.008 and 0.018 inches. The axial length of the primary coil will usually fall in the range of 0.5 to 100 cm, more usually 2.0 to 40 cm. Depending upon usage, the coil may well have 10–75 turns per centimeter, preferably 10–40 turns per centimeter. All of the dimensions here are provided only as guidelines and are not critical to the claimed invention. However, only dimensions suitable for use in occluding sites within the human body are included in the scope of this invention. These specifications are set forth only for the purposes of example, and the invention is not limited in any way by virtue of coil sizes or structure.

Figure 3A:
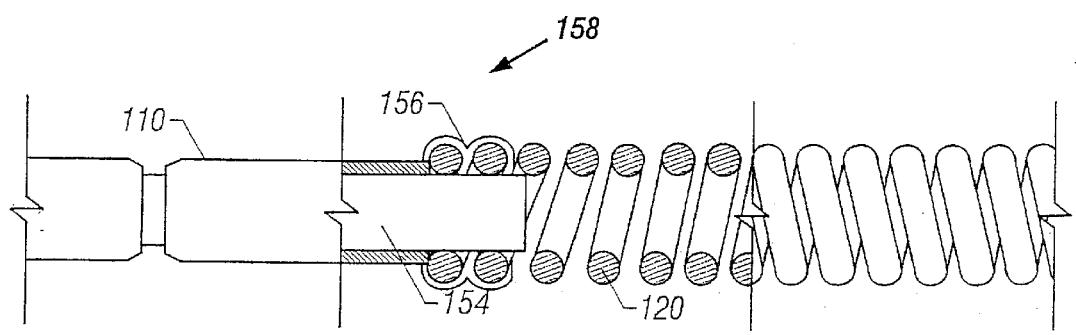

FIG. 3a shows an embodiment (158) of the inventive implant assembly. In this embodiment, implant (120) is attached to core wire (110) and at the same time is electrically insulated from the metallic center (154) of core wire (110) by the use of a nonconducting glue or thermopolymer (156) made from a suitable polymer, e.g., a thermoplastic. Both the use of solid insulation and a layer is contemplated as the material for forming the electrical isolation of implant (120) are contemplated. Such a layer may be plated, sputtered, painted, heat shrunk, glued, or melted onto the appropriate part.

Figure 3B:
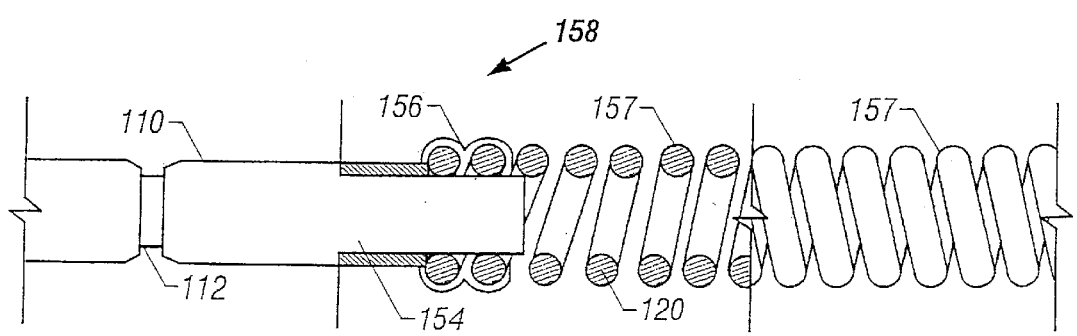

FIG. 3b is identical to FIG. 3a except wire (110) may be soldered or connected in a conventional manner to implant (120) so that they are electrically coupled and except implant (120) has been coated with a thin insulative coating (157) on all exposed surfaces, including both the exterior surfaces of the coil comprising implant (120) as well as its interior surfaces. Joint (112) continues to remain exposed and uncoated. All other distal portions of wire (110) remain insulated by insulation (111) or may be coated as well with coating (157). In this manner, implant (120) is isolated from or protected against electrolysis by virtue of being in contact with the blood or ionic fluid, while implant (120) is still electrically connected to wire (110). The same advantageous effect of restricting the electrolytic current to joint (112) is realized and the same current densities are achieved as in the embodiment of FIG. 2 or 3a. As a result, the same fast detachment times discussed below are achieved.

The number of examples in which the invention could be illustrated can be multiplied almost endlessly. Many of additional examples are shown, for example, in PCT-International Patent Application WO 99/09894. The particular specifics by which the invention claimed below can be variously realized do not form part of the claimed invention which is the broader concept claimed below. The descriptions set forth above have therefore been set forth only to give a few illustrations of how the invention can be realized and do not define the invention by way of limitation.

Figure 4:
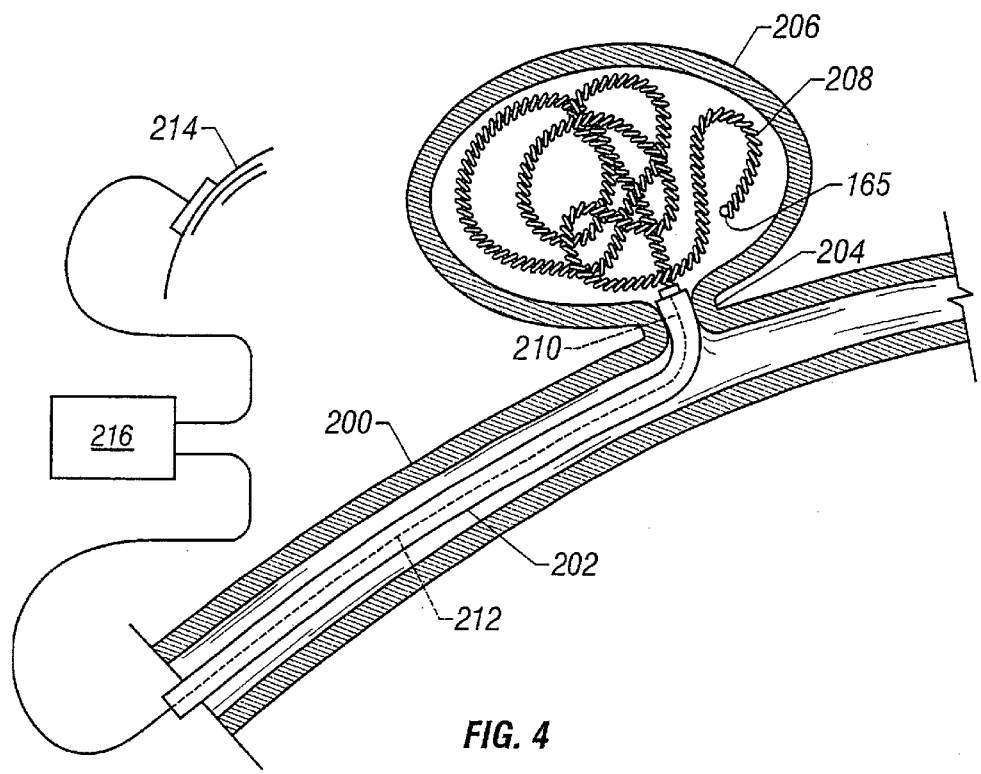
FIGS. 4 and 5 show, in schematic form, a procedure for deploying the inventive vaso-occlusive device of this invention.
Figure 5:
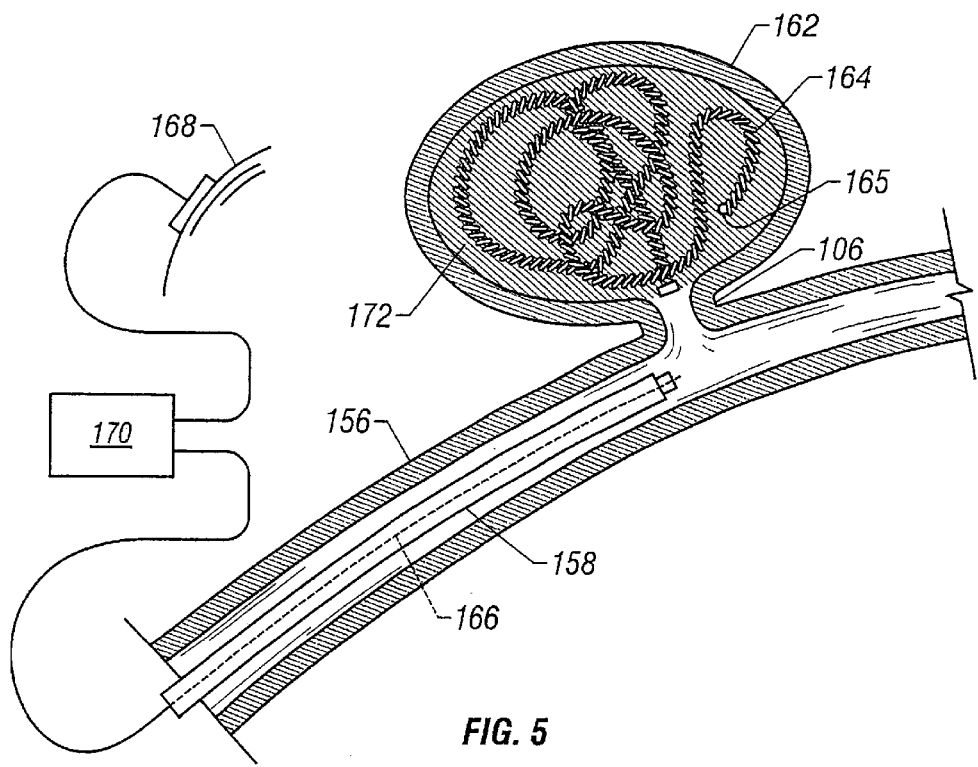

FIGS. 4 and 5 show placement of the devices, specifically the vasoocclusive embodiments of the invention, within the human body. FIG. 4 shows the placement within a vessel or artery (200) with a tip of catheter (202) placed near aneurysm neck (204). The aneurysm itself is referenced by numeral (206). Vaso-occlusive device (208) is disposed into aneurysm (206) at least until the sacrificial link or joint (210) (hidden within catheter (202) at this step) is exposed beyond the distal tip of catheter (202). An embolic mass is then formed within aneurysm (206). A positive electric current of approximately 0.01–2 milliamps at 0.1–12 or more volts as applied to core wire (212). The negative pole (214) of power supply (216) is typically placed in electrical contact with the skin so to complete the circuit. The vaso-occlusive device (208) is detached from core wire (212) by electrolytic disintegration of sacrificial link (210).

After sacrificial link (210) is at least mostly dissolved by electrolytic action, typically in less than two minutes and most often in less than one minute, the core wire (212), catheter (202), are removed from vessel (200) leaving aneurysm (206) occluded as shown in FIG. 5.

This procedure is typically practiced under fluoroscopic control with local or general anesthesia. A transfemoral catheter may be used to treat cerebral aneurysm and is usually introduced at the groin. When the vaso-occlusive device (208) is isolated by a highly resistive material as is contemplated this invention, it is not affected by electrolysis. When the core wire (212) and the pertinent portions of the supporting coils at the distal tip of the core wire (when utilized) are adequately coated with insulating coverings, only the exposed portion of the sacrificial link (210) is affected by the electrolysis.

The following experiment has been run by Target Therapeutics on the claimed invention to demonstrate the effectiveness of isolating implant (120) from electrolytic action. Detachment times for commercially available devices manufactured by Target Therapeutics in which implant (120) is electrically coupled to wire (110) and hence is subject to electrolytic action, were compared with those for a embodiment of the invention similar to that shown in FIG. 2. There were two sets of ten implant assemblies. The first set (FIG. 6) were commercial GDC assemblies as modified below to simulate multiple coil placement. The second set (FIG. 7) were similar to those described in regard to FIG. 2 incorporating a PET insulator between the detachable coil and the electrolytic joint. The implants on each were platinum coils.

To exaggerate and lengthen the detachment times for each set, as would be the case when an implant is inserted into an aneurysm already having a number of platinum coils with vestigial remaining stainless steel stubs remaining from prior detachments and having electrical contact with those coils, an additional stainless steel wire of about one inch length was added to the detachable coils. The resulting detachment times for the coils were increased by as much as ten-fold as is sometimes seen clinically.

Figure 6:
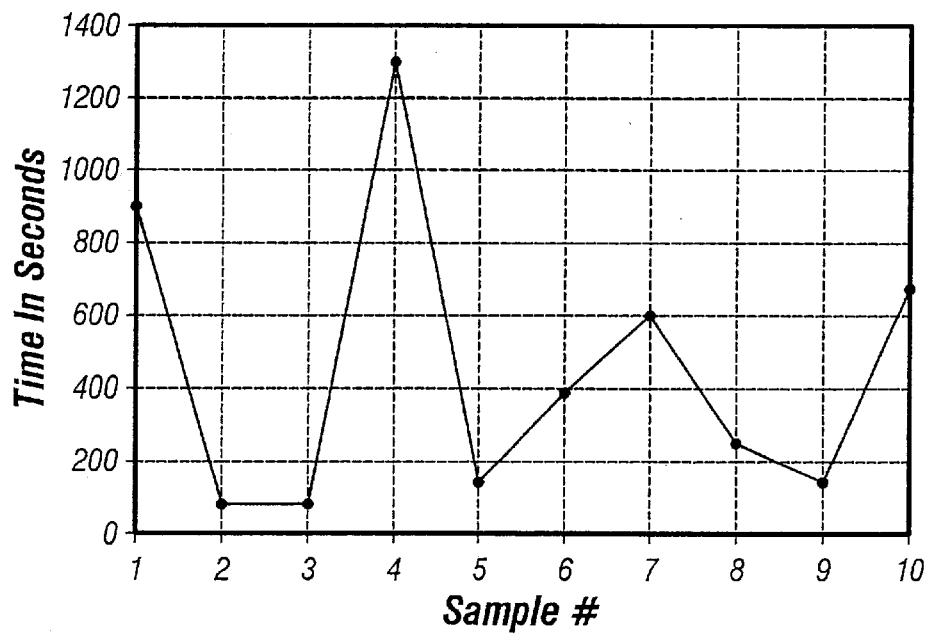
FIG. 6 is a graph of detachment times for a comparative commercial GDC device.
Figure 7:
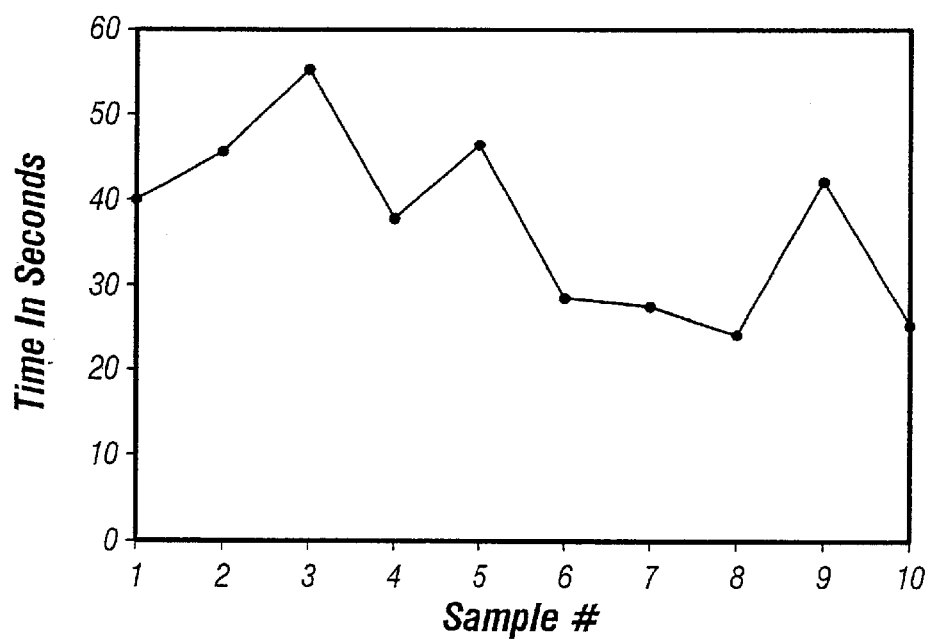
FIG. 7 is a graph of detachment times for embodiments of the GDC device made according to the invention.

Each of the sets were placed in a saline bath and subjected to a constant amperage of 1 ma and a resulting voltage of between 1.5 and 2.0 volts. The time for electrolytic erosion of the joint was measured. As shown in FIG. 6, the average time for detachment of the commercial GDC coil was 454.9 seconds. As shown in FIG. 7, the average time for detachment of the inventive embodiment GDC coil using a PET insulator sock was 38 seconds.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An implant assembly for placement of an implant member in the human body in presence of an ionic fluid comprising:
    said implant member having a proximal end and a distal end, and
    an electrolytically severable joint situated to release said implant member upon application of electrical energy to said electrolytically severable joint,
    wherein said implant member is electrically isolated from electrolysis in said ionic fluid,
    wherein said electrical isolation from electrolysis is due to an insulative or highly resistive layer interposed between implant member and said electrolytically severable joint.

2. The implant assembly of claim 1 wherein said insulative or highly resistive layer comprises a polymer.

3. The implant assembly of claim 2 wherein said insulative or highly resistive layer comprises polyester.

4. An apparatus for occluding a body cavity in the presence of an ionic fluid comprising:
    a wire having a proximal and distal end, said distal end being adapted to be positioned in or near said body cavity, said distal end of said wire being fully insulated except for a selected portion serving as an electrolytic joint;
    a detachable implant coupled to said distal end of said wire, distal from said joint, said implant adapted to be positioned in said body cavity, said implant being electrically isolated from electrolysis in said ionic fluid, where substantially only said joint is electrolyzed when current is applied to said wire,
    wherein said implant is electrically isolated from electrolysis in said ionic fluid by electrical isolation from said wire.

5. The apparatus of claim 4 wherein said implant is electrically isolated from said wire by interposition of an insulator between said wire and said implant.

6. The apparatus of claim 5 where said insulator interposed between said wire and implant is polyester.

7. An apparatus for occluding a body cavity in the presence of an ionic fluid comprising:
    a wire having a proximal and distal end, said distal end of said wire being insulated;
    an electrolytic joint coupled to said distal end, said electrolytic joint being insulated at least in part;
    a detachable implant coupled to said electrolytic joint, said implant not being subject to electrolysis in said ionic fluid when current is applied to said wire, and where said joint is electrolyzed when current is applied to said wire to separate said implant from said wire
    wherein said implant is not subject to electrolysis in said ionic fluid by virtue of electrical isolation of said implant from said wire.

8. The apparatus of claim 7 wherein said implant is electrically isolated from said wire by interposition of an insulator between said wire and said implant.

9. The apparatus of claim 8 where said insulator interposed between said wire and implant is polyester.

* * * * *